United States Patent
Hahn

(10) Patent No.: US 6,856,825 B2
(45) Date of Patent: *Feb. 15, 2005

(54) MEDICAL APPARATUS

(75) Inventor: Guenter Hahn, Shanghai (CN)

(73) Assignee: SIEMENS Aktiengesellschaft, Munich (DE)

( * ) Notice: Subject to any disclaimer, the term of this patent is extended or adjusted under 35 U.S.C. 154(b) by 282 days.

This patent is subject to a terminal disclaimer.

(21) Appl. No.: 09/960,383

(22) Filed: Sep. 24, 2001

(65) Prior Publication Data

US 2002/0049562 A1 Apr. 25, 2002

(30) Foreign Application Priority Data

Sep. 22, 2000 (DE) .......................................... 100 47 552

(51) Int. Cl.[7] ................................................. A61B 5/05
(52) U.S. Cl. ........................ 600/425; 600/407; 702/183; 702/184; 702/185
(58) Field of Search ................................ 600/407, 425; 705/2; 345/762, 765; 128/920, 925; 702/183, 184, 185, 186, 188

(56) References Cited

U.S. PATENT DOCUMENTS

| | | | | |
|---|---|---|---|---|
| 4,803,639 A | * | 2/1989 | Steele et al. | 702/40 |
| 5,353,238 A | | 10/1994 | Neef et al. | |
| 5,603,323 A | * | 2/1997 | Pflugrath et al. | 600/437 |
| 5,812,397 A | * | 9/1998 | Pech et al. | 700/81 |
| 6,509,914 B1 | * | 1/2003 | Babula et al. | 345/762 |
| 6,675,131 B2 | * | 1/2004 | Hahn | 702/188 |
| 2003/0065308 A1 | * | 4/2003 | Lebel et al. | 604/891.1 |

FOREIGN PATENT DOCUMENTS

| | | |
|---|---|---|
| DE | 36 09 927 A1 | 10/1987 |
| DE | 42 34 654 A1 | 4/1994 |
| DE | 196 50 569 A1 | 6/1998 |
| WO | WO 87/06045 | 10/1987 |
| WO | WO 98/25396 | 6/1998 |

* cited by examiner

Primary Examiner—Eleni Mantis Mercader
(74) Attorney, Agent, or Firm—Young & Thompson

(57) ABSTRACT

A medical apparatus for dealing with problems which, when a problem affecting the medical apparatus occurs, determine the component (7) which is the cause of the problem concerned and display it, in the event that this is a component (7) which can be exchanged by an apparatus user without service support, the means for dealing with problems (13) displaying a request to exchange this component.

17 Claims, 2 Drawing Sheets

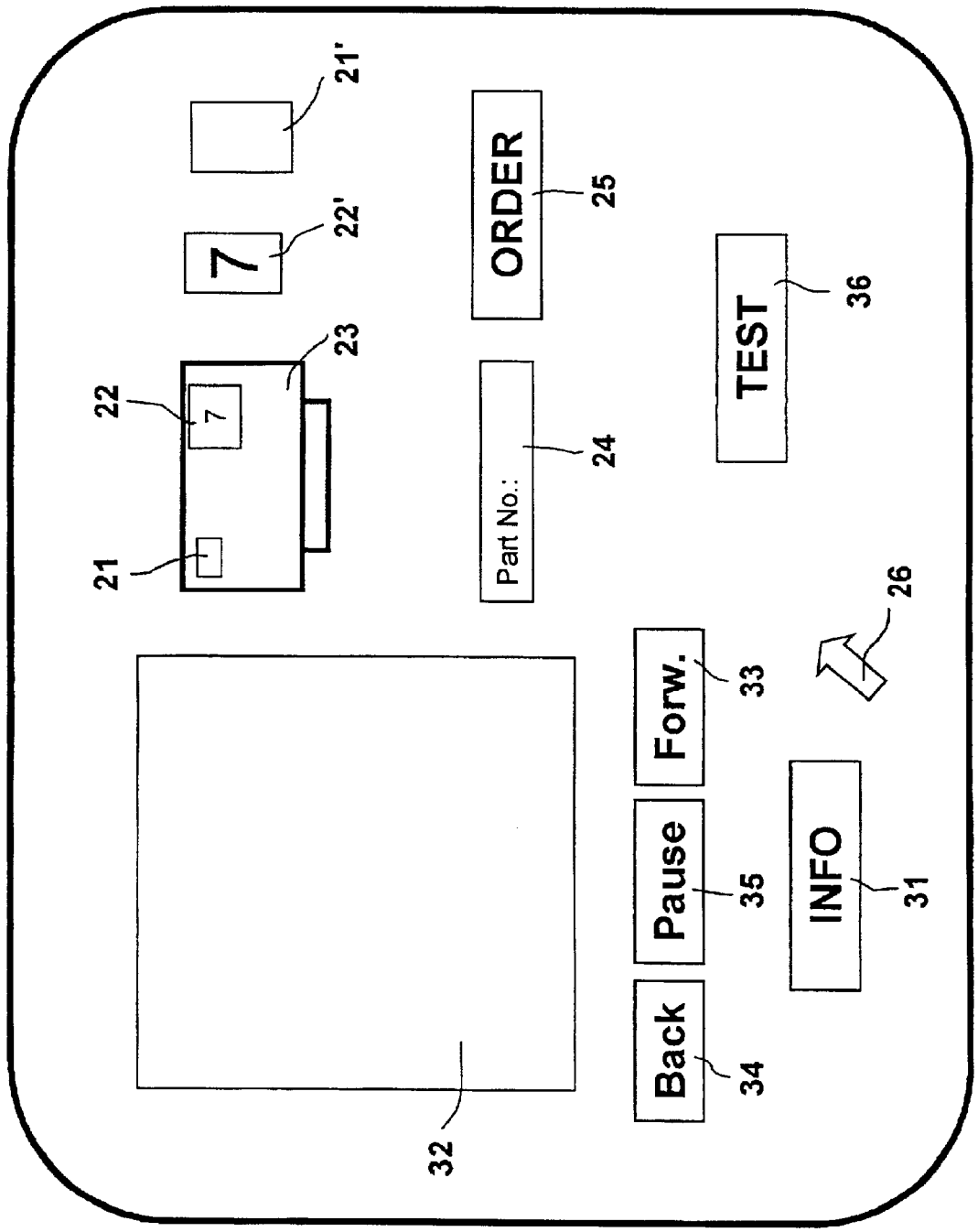

MEDICAL APPARATUS

BACKGROUND OF THE INVENTION

The invention relates to a medical apparatus with means for dealing with problems.

DESCRIPTION OF THE RELATED ART

For dealing with problems, medical apparatuses that are currently commercially available have comprehensive self-test programs, which in some circumstances can be activated or interrogated by telecommunication or remote access means. Furthermore, generally extensive service documents are available.

However, appropriately trained personnel are usually required in order to allow the means of assistance respectively available for dealing with problems to be correctly applied, the test results to be evaluated and defective parts to be repaired or exchanged.

SUMMARY OF THE INVENTION

The invention is based on the object of designing a medical apparatus of the type stated at the beginning in such a way that the training measures required for dealing with problems can be less expensive.

According to the invention, this object is achieved by a medical apparatus with means for dealing with problems which, when a problem affecting the medical apparatus occurs, determine that (those) component(s) which is (are) the cause of the problem concerned and display it (them) on a display device. On account of the fact that components causing the respective problem are determined and indicated by the apparatus itself, the effort for the persons involved in dealing with a problem is so small that the apparatus user himself, i.e. the physician or a medical assistant, can act on dealing with the problem.

According to a variant of the invention, it is provided that the means for dealing with problems obtain problem-specific data on the medical apparatus with respect to the problem determined and evaluate them with regard to the component(s) causing the problem concerned, the apparatus preferably containing a data memory in which information serving for determining data is stored and taken from the data memory by the means for dealing with the problem on a problem-dependent basis. In this way, a problem-related and reliable functioning of the means for dealing with problems is ensured, although no specially trained person is involved in dealing with the problem.

According to a particularly preferred embodiment of the invention, it is provided that at least one of the components of the medical apparatus is what is known as a self-change component, i.e. a component which can be exchanged by an apparatus user without service support, and that, in the event that a self-change component is a component causing the problem concerned, the means for dealing with problems display a request to exchange this self-change component.

In this case, the exchange is particularly easy and reliable if, according to a variant of the invention, the self-change components are provided with a visible code and the means for dealing with problems indicate the code of a self-change component when they display a request to exchange such a component.

It is likewise advantageous in the interests of the reliable and easy exchange of self-change components if, according to one embodiment of the invention, the medical apparatus contains a data memory in which illustrations of the self-change components are stored, the means for dealing with problems displaying the illustration of a self-change component when they display a request to exchange such a component.

To avoid errors when ordering a self-change component to be exchanged, a variant of the invention provides that the means for dealing with problems order the self-change component to be exchanged via telecommunication means, for example from the apparatus manufacture itself or a service center.

To avoid errors when exchanging self-change components, it is provided according to variants of the invention that self-change components are designed in a way ensuring that they cannot be mixed up or the connections of self-change components serving for power and/or signal transmission are designed in a way ensuring that they cannot be mixed up.

In order to ensure proper operation of the medical apparatus after a component has been exchanged, in particular a self-change component, it is provided that the means for dealing with problems perform a test on the medical apparatus after the exchange of a component and only authorize normal operation of the apparatus if there is a positive test result, the medical apparatus preferably containing a data memory in which information serving for carrying out the test is stored and taken from the data memory by the means for dealing with the problem according to the component respectively exchanged, so that it is ensured that the test is conducted on a problem-related basis without a person acting on dealing with the problem having to have special knowledge.

In order to reduce further the risk of errors during the exchange of self-change components, the apparatus is assigned a data memory in which at least partially graphic information concerning the exchange of self-change components which can be presented on a display unit of the apparatus is stored, for example in the form of exploded representations, series of photographs or video sequences.

BRIEF DESCRIPTION OF THE DRAWINGS

An exemplary embodiment of the invention is represented in the attached schematic drawings, in which:

FIG. 3 shows a display occurring on the display device of the CT apparatus according to the invention during operation of the latter.

DESCRIPTION OF THE PREFERRED EMBODIMENTS

Figure 1:
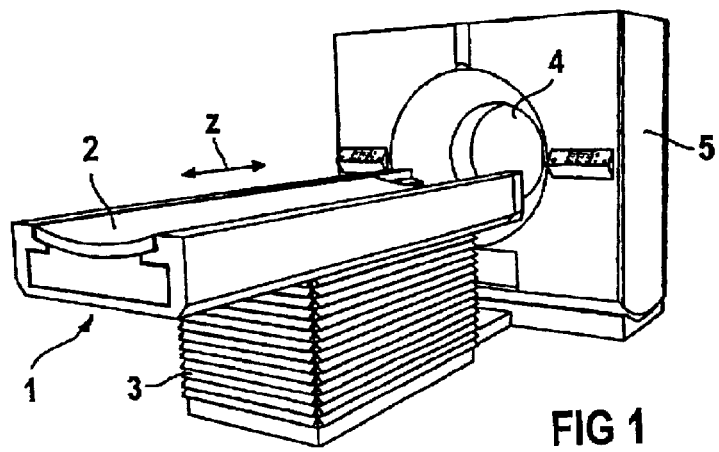
FIG. 1 shows a CT apparatus according to the invention in a perspective representation.

Represented in FIG. 1 is a medical apparatus according to the invention, the apparatus concerned being a CT apparatus which has a patient-supporting table 1 with a supporting plate 2, which can be displaced in the direction of the double-headed arrow z, in the direction of its longitudinal axis parallel to the system axis of the CT apparatus and which, in the case of the exemplary embodiment described, is attached on a base 3 in a vertically adjustable manner, but alternatively may also be attached in a fixed manner.

An object under investigation lying on the supporting plate 2, for example a patient 11 (see FIG. 2), can be positioned into the measuring opening 4 of a measuring unit 5 by a corresponding longitudinal displacement of the supporting plate 2.

Figure 2:
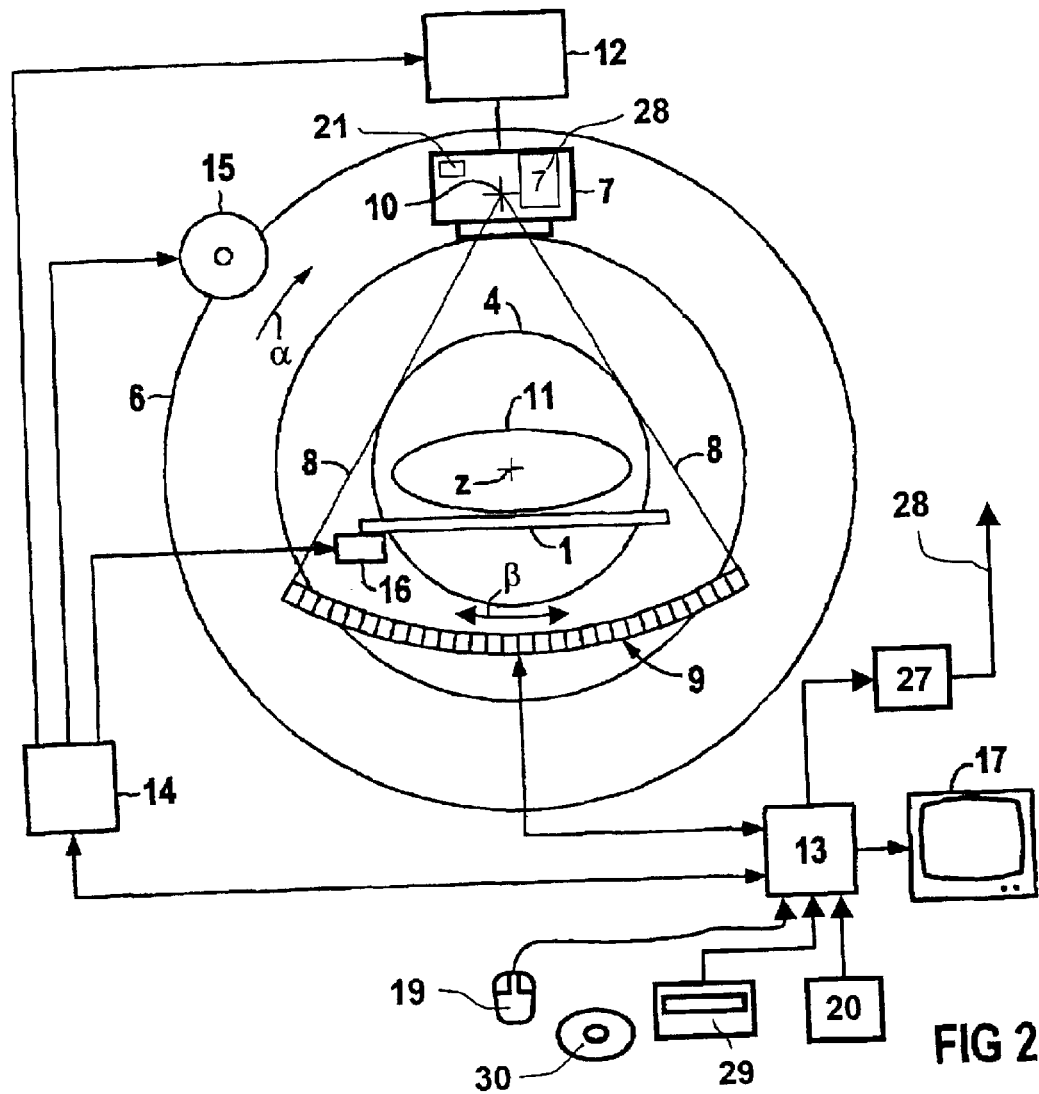
FIG. 2 shows the CT apparatus according to FIG. 1 in a schematic, partially block-diagram-like representation.

As can be seen from FIG. 2, the measuring unit includes a ring mount 6 which surrounds the measuring opening 4 and on which an X-ray radiation source 7 and a detector system 9 are arranged lying opposite each other, the detector system in the case of the exemplary embodiment described being formed by a row of, for example, 512 detector elements curved in the form of an arc of a circle, each detector element being assigned a channel angle β.

The X-ray radiation source 7 has a focus, denoted by 10, from which there emerges a fan-shaped X-ray radiation beam 8 impinging on the detector system 9.

Connected to an electronic computing device 13 is a display device 17, provided for the display of section images. Also connected to the electronic computing device 13 is an input instrument, in the case of the exemplary embodiment represented a mouse 19, which allows the CT apparatus to be operated on the basis of graphic operator-control menus which can be presented on the display device 17.

For controlling the rotary movement of the ring mount 6, the longitudinal movement of the supporting plate 2 and the X-ray radiation source 7, a control unit 14 is provided, activating the drives 15 and 16 assigned to the ring mount and the supporting plate 2 and also activating the high-voltage generator 12.

For scanning a patient 11 lying on the supporting plate 2, the ring mount 6 is turned in the α direction about the system axis z running centrally through the measuring opening 4 and at right angles to the plane of the drawing of FIG. 2, to be precise in such a way that the focus 10 of the X-ray radiation source 7 moves on a circular path which lies in a plane at right angles to the system axis. As this happens, the fan-shaped X-ray radiation beam 8 emerging from the X-ray radiation source 7 fed by a high-voltage generator 12 irradiates a planar layer of the patient 11 running at right angles to the system axis 2.

At predetermined angular positions, known as the projection angles α, the output signals of the detector elements of the detector system 9 corresponding to the corresponding projections are fed to the electronic computing device 13, which computes from these the attenuation values belonging to the individual detector elements, and consequently channel angles β, of the layer of the patient 11 detected by the X-ray radiation beam 8.

Since the supporting plate 2 is displaceable in the direction of the system axis z, a volume of the patient 11 can be scanned by either the supporting plate 2 being continuously displaced during continuous rotation of the measuring unit 5 (known as spiral scanning) or by the supporting plate 2 being displaced step by step in such a way that a number of parallel layers, preferably adjacent to one another, are scanned one after the other (known as sequence scanning). The sets of attenuation values corresponding to the projections thereby recorded are fed to the electronic computing device 13, which determines section images from these sets of values on the basis of reconstruction algorithms known per se and, as mentioned, displays them on the display device 17.

The electronic computing device 13 also performs the function of means for dealing with problems which, in the case of a problem occurring during the operation of the CT apparatus, for example an operating fault or a malfunction, determines that (those) component(s) which is (are) the cause of the problem concerned and display it (them) on the display device 17.

For this purpose, connected to the electronic computing device 13 is a data memory 20, in which there is stored information which enables the electronic computing device 13 to obtain problem-specific data on the CT apparatus with respect to the problem respectively concerned, which the electronic computing device 13 evaluates with regard to the components(s) causing the problem respectively concerned. Said information is stored in the data memory 20 on a problem-related basis, so that the electronic computing device 13 can take the required information on a problem-dependent basis and consequently in fact only has to obtain those data on the medical apparatus that are essential for the problem respectively concerned.

Some of the components of the CT apparatus according to the invention are known as self-change components, i.e. components which can be exchanged by the apparatus user himself, without any need to call on the assistance of specially trained service personnel. In the case of the exemplary embodiment described, such components are the X-ray radiation source 7, the detector system 9, the high-voltage generator 12 and air filters not represented in the figures. As shown in FIG. 2 only for the X-ray radiation source 7, for reasons of overall clarity, the self-change components are provided with a color and number code, i.e. each self-change component has a color zone 21 and an inscription zone 22, as illustrated in the case of the X-ray radiation source 7, the color code being applied in the respective color zone and the number code being applied in the respective inscription zone. In the case of the X-ray radiation source 7 in the present exemplary embodiment, the number code applied in the inscription zone 22 of the X-ray radiation source 7 coincides with the reference number of the X-ray radiation source 7.

The color and number codes belonging to the individual self-change components and icon-like illustrations of the self-change components are likewise stored in the data memory 20.

If a problem occurs in the case of the CT apparatus according to the invention, the electronic computing device 13 presents the screen mask represented in FIG. 3 on the display device 17 if it has determined one of the self-change components as the cause of the problem, FIG. 3 representing the situation in the case where the X-ray radiation source 7 is the self-change component causing a problem which has occurred.

Accordingly, the electronic computing device 13 displays in accordance with the color and number code of the X-ray radiation source 7 this color and number code in a color zone 21' and an inscription zone 22'. Furthermore, the electronic computing device 13 displays the icon 23 illustrating the X-ray radiation source 7.

In addition, the electronic computing device 13 displays a text zone 24, with the part number of the respective self-change component, likewise stored in the data memory 20, and a button 25 provided in FIG. 3 with the designation ORDER.

If the mouse pointer 26 is moved onto the button 25 and is double clicked, the electronic computing device 13 orders the required self-change component, that is in the present case the X-ray radiation source 7, from the manufacturer of the CT apparatus via telecommunication means connected to said device, in the case of the exemplary embodiment described a modem 27 connected to a data line, for example a telephone line 28, and for this purpose transmits to the manufacturer of the CT apparatus in addition to the part number all the data necessary for executing the order, such as for example the location of the CT apparatus, customer number, etc. The electronic computing device 13 likewise takes these data from the data memory 20, in which these data are also stored.

When the self-change component arrives, the apparatus user can call up information on the installation of the respective self-change component by moving the mouse pointer 26 onto a button designated 31 and double clicking it. In the case of the exemplary embodiment represented, the electronic computing device 13 then accesses a CD-ROM drive 29, in which a CD-ROM 30 containing the corresponding information is located, this information being presented by the electronic computing device 13 on the screen of the display device 17 in a display zone 32.

The information stored on the CD-ROM 30 takes the form of exploded drawings and/or series of drawings or photographs and/or video sequences.

The information presented in the display zone 32 allows the apparatus user to navigate by means of three buttons 33 to 35, moving forward in the information by means of the button 33 designated Forw. and moving backward by means of the button 34 designated Back. The button 35 designated Pause serves in the case where video sequences are displayed for presenting a specific image of the video sequence as a still picture.

Once the exchange of the respective self-change component has taken place, the electronic computing device 13 carries out a test of the CT apparatus in response to actuation of a button 36 designated TEST by means of the mouse pointer 26. The information required for tests to be carried out is stored in the data memory 20, from which the electronic computing device 13 takes the respectively required information in accordance with the tests to be carried out after the self-change component respectively concerned has been exchanged.

In the case of a positive test outcome, the electronic computing device 13 again presents on the display device 17 a menu serving for the operation of the CT apparatus, while in the case of a negative test outcome it displays a request to make contact with service personnel of the apparatus manufacturer, the possibility of contacting the service personnel via the modem 27 being provided by actuating a corresponding button.

In the case of the exemplary embodiment described, the data memory 20 and the modem 27 and the CD-ROM drive 29 are represented as separate components. These may, however, also be integrated into the electronic computing device 13.

In the case of the exemplary embodiment described, the self-change components are provided with a color and number code, but it is also possible for only a color code or only a number code to be provided. Furthermore, a letter code may be provided instead of the number code.

In the case of the exemplary embodiment described, the data traffic between the modem 27 and the manufacturer of the CT apparatus takes place in a wire-bound manner over the telephone network. Instead of this, the connection may also take place wirelessly over a mobile radio network. Furthermore, in the case of the data exchange between the CT apparatus and the manufacturer of the CT apparatus, the possibilities of the Internet, in particular the World Wide Web, can be utilized.

A problem in which the exchange of only one self-change component is required is described above. Depending on the problem occurring, it may also be possible, however, to exchange a number of self-change components, the electronic computing device 13 additionally presenting the corresponding data and information on the display device 17.

As a departure from the above procedure for ordering a self-change component to be exchanged, it may also be envisaged that it is sufficient to click on the icon representing it to send the order. It is then possible to dispense with the button 25.

To rule out errors in the case of exchanging self-change components, they, and similarly their connections serving for power and/or signal transmission, are designed in a way not represented in the figures such that they cannot be mixed up, so that neither self-change components can be inadvertently mixed up, that is for example an X-ray radiation source cannot be fitted instead of a detector, nor can the connections be mixed up, that is the connection of the X-ray radiation source cannot be fitted at the connection of the CT apparatus intended for the detector.

Moreover, it may be provided that the CT apparatus automatically detects and reminds of the necessity for changing or supplying consumable material, such as for example the necessary exchange of filters or of the X-ray radiation source.

It is clear that the invention opens up the possibility for the apparatus user to deal with problems and perform parts of the servicing procedure himself: in the case of technical problems, the apparatus can identify and name defective components in an intelligent self-test. Self-change components have a color or number code, with the aid of which the defective self-change component can be localized by the apparatus user. In addition to an illustration of the module, ordering information is displayed on the display device. The self-change component to be replaced can consequently be ordered directly. The exchange of self-change components is presented in a graphically illustrated and intelligible way on a CD-ROM which is included in the accessories supplied with the apparatus. The apparatus user can easily exchange the defective self-change component himself.

However, it is also possible not to provide a purely self-conducted test but a guided test (the apparatus user is guided step by step through the test), the data obtained by this test serving for determining the components causing a problem. In this case, it may be necessary for a service center to provide assistance, for example by telephone, when determining the components causing a problem.

The invention is described above by the example of a CT apparatus; it may, however, be used in the case of any other medical apparatuses.

What is claimed is:

1. A medical imaging apparatus comprising:
   means for dealing with problems which, when a problem affecting the medical imaging apparatus occurs, self-determines, free of medically trained user input, that (those) component(s) which is (are) the cause of the problem concerned and display it (them) on a display device,
   at least one of the components of which is a self-change component which can be exchanged by an apparatus user without service support and, in the event that a self-change component is a component causing the problem concerned, the means of which for dealing with problems display a self-initiated request to exchange this self-change component, and
   in which the means for dealing with problems order the self-change component to be exchanged via telecommunication means, wherein the apparatus user is a physician or an imaging apparatus trained medical assistant.

2. The medical imaging apparatus as claimed in claim 1, the means of which for dealing with problems obtain problem-specific data on the medical imaging apparatus with respect to the problem determined and evaluate them with regard to the component(s) causing the problem concerned.

3. The medical imaging apparatus as claimed in claim 2, which contains a data memory in which information serving for determining data is stored and taken from the data memory by the means for dealing with the problem on a problem-dependent basis.

4. The medical imaging apparatus as claimed in claim 1, the self-change components of which are provided with a visible code and the means of which for dealing with problems indicate the code of a self-change component when they display a request to exchange such a component.

5. The medical imaging apparatus as claimed in claim 1, which contains a data memory in which illustrations of the self-change components are stored, and in which apparatus the means for dealing with problems display the illustration of a self-change component when they display a request to exchange such a component.

6. The medical imaging apparatus as claimed in claim 1, in which self-change components are designed in a way ensuring that they cannot be mixed up.

7. The medical imaging apparatus as claimed in claim 1, wherein the self-change components include any one of an x-ray radiation source, a radiation detector system, and a high-voltage generator.

8. The medical imaging apparatus as claimed in claim 1, in which the means for dealing with problems perform a test on the medical imaging apparatus after the exchange of a component and only authorize normal operation of the apparatus if there is a positive test result.

9. The medical imaging apparatus as claimed in claim 8, which contains a data memory in which information serving for carrying out the test is stored and taken from the data memory by the means for dealing with the problem according to the component respectively exchanged.

10. The medical imaging apparatus as claimed in claim 1, the apparatus being assigned a data memory in which at least partially graphic information concerning how to user-exchange the self-change components which graphic information can be presented on a display unit of the apparatus is stored.

11. The medical imaging apparatus, comprising:
plural components operatively connected to perform a medical function; and
self-test means for independently determining, free of medically trained user input, through an intelligent self-test when a problem affecting the medical imaging apparatus occurs, a problem-causing component from among the plural components, and displaying the problem-causing component on a display device,
the problem-causing component being a self-change component which can be exchanged by an apparatus user without service support,
wherein the apparatus user is a physician or an imaging apparatus trained medical assistant.

12. The medical imaging apparatus of claim 11, wherein the self-test means is interfaced with problem-specific data relating to the components of the medical imaging apparatus with respect to the problem and evaluate the problem with regard to the problem-causing component.

13. The medical imaging apparatus of claim 12 wherein the plural components include any one of an x-ray radiation source, a radiation detector system, and a high-voltage generator.

14. The medical imaging apparatus of claim 13, wherein the self-change component is provided with a visible code and the self-test means indicates the code of a self-change component when displaying the problem-causing component.

15. The medical imaging apparatus of claim 13 further comprising stored illustrations of the self-change component interfaced to the self-test means, wherein the stored illustrations display an illustration of the self-change component when displayed as the problem-causing component.

16. The medical imaging apparatus of claim 13, wherein the self-test means comprises an ordering part for ordering the problem-causing component via a telecommunications link.

17. The medical imaging apparatus of claim wherein the self-test means comprises a post-installation test to perform a diagnostic test on the medical imaging apparatus after the exchange of the problem-causing component to verify proper post-installation operation of the medical imaging apparatus.

* * * * *